(12) United States Patent
Itai et al.

(10) Patent No.: US 8,923,614 B2
(45) Date of Patent: Dec. 30, 2014

(54) IMAGE PROCESSING APPARATUS, IMAGE PROCESSING METHOD

(71) Applicant: Hitachi High-Technologies Corporation, Tokyo (JP)

(72) Inventors: Hideki Itai, Hitachinaka (JP); Zhigang Wang, Hitachinaka (JP); Kazunari Asao, Naka (JP)

(73) Assignee: Hitachi High-Technologies Corporation, Tokyo (JP)

( * ) Notice: Subject to any disclaimer, the term of this patent is extended or adjusted under 35 U.S.C. 154(b) by 110 days.

(21) Appl. No.: 13/791,469

(22) Filed: Mar. 8, 2013

(65) Prior Publication Data

US 2013/0343649 A1 Dec. 26, 2013

(30) Foreign Application Priority Data

Jun. 22, 2012 (JP) ................. 2012-141083

(51) Int. Cl.
*G06K 9/34* (2006.01)
*G06K 9/46* (2006.01)
*G06T 5/00* (2006.01)
*G01N 23/225* (2006.01)

(52) U.S. Cl.
CPC .......... *G06K 9/4647* (2013.01); *G01N 2223/42* (2013.01); *G06T 2207/10061* (2013.01); *G06T 5/007* (2013.01); *G01N 23/2254* (2013.01)
USPC ........................................................ 382/169

(58) Field of Classification Search
None
See application file for complete search history.

(56) References Cited

U.S. PATENT DOCUMENTS

| 7,935,275 | B2 * | 5/2011 | Miyoshi et al. | ............... 252/502 |
| 2005/0218325 | A1 * | 10/2005 | Nishiyama et al. | ........... 250/311 |
| 2006/0199903 | A1 * | 9/2006 | Miyoshi et al. | ............. 525/92 B |
| 2010/0297362 | A1 * | 11/2010 | Budach et al. | ................ 427/585 |

FOREIGN PATENT DOCUMENTS

JP 2004-208044 A 7/2004

* cited by examiner

*Primary Examiner* — Sean Motsinger
(74) *Attorney, Agent, or Firm* — McDermott Will & Emery LLP

(57) ABSTRACT

In order to solve the problem that the resolution of a back-scattered electron image without a contrast difference between materials with close atomic numbers is low, an image processing apparatus that performs an image process on a back-scattered electron image as an input image includes: a material peak detection unit that determines a peak luminance value with a peak of a frequency of a luminance histogram based on a luminance value obtained for each measurement position by using the input image as an input and information about material-dependent back-scattered electron generation efficiency, and that outputs the peak luminance value for each material; and an image information adjustment unit that emphasizes a material-dependent contrast on the basis of the input image and the peak luminance value for each material.

9 Claims, 8 Drawing Sheets

Back-scattered electron image 21

Measurement object pattern 22

Non-measurement area 23

Diameter (size)

(Histogram)

IMAGE PROCESSING APPARATUS, IMAGE PROCESSING METHOD

BACKGROUND

1. Technical Field

Embodiments discussed herein generally relate to an image processing technology.

2. Related Art

Observation of fine patterns is required in various fields, such as semiconductor manufacturing and medical fields. For example, in the semiconductor manufacturing field, semiconductor devices and the like have been integrated or decreased in size to increasingly higher degrees, and improvements in performance of charged particle beam apparatuses for observing and measuring such samples are desired. For example, in a scanning electron microscope (hereafter referred to as "SEM"), which is a type of charged particle beam apparatus, high resolution and reproducibility are required. Also, in order to achieve high resolution and reproducibility, contrast and brightness of an image for sample observation, measurement, or inspection by the SEM need to be properly adjusted, and there is a room for improvement in relevant image processing technology.

Signal electrons that are emitted by excitation of atoms at the surface of an observed sample upon irradiation with an electron beam and that have low energy are referred to as "secondary electrons". When an edge portion of a sample pattern with convex-concave, such as a semiconductor circuit pattern, is irradiated with an electron beam, the amount of secondary electron generated is increased by an edge effect, resulting in an image with an irregularity-dependent contrast.

Electrons that are re-emitted from the sample surface in the process of scattering of the electron beam within the sample are referred to as "back-scattered electrons". The back-scattered electrons are signal electrons with high energy. The back-scattered electrons provide an image with a contrast that depends on the sample (material) composition, rather than the convex-concave of the sample.

In recent years, due to the increasingly complex processes for semiconductors, magnetic heads and the like, measuring of low-step samples with no convex-concave on the observed sample surface is required. In this case, the amount of secondary electron signal that is detected is decreased because of the low step. Thus, improved image quality and length measurement accuracy can be obtained by detecting the back-scattered electrons instead of, or together with, the secondary electrons, and by enhancing the edge or contrast information by composing a signal or image on the basis of the back-scattered electrons. Detection through the back-scattered electrons is also possible even when a barrier for the secondary electrons is formed by charging of the surface of a sample, such as a sample containing insulator material, on the order of several to several dozens of volts due to the irradiation by the electron beam during SEM observation. Because the contrast of a back-scattered electron image is determined depending on the atomic number of the material, a sharp image can be obtained from a pattern of materials with a large atomic number difference.

JP Patent Publication (Kokai) No. 2004-208044 A discloses a contrast and brightness adjustment method for obtaining an appropriate gradation. The method involves acquiring a bright image and a dark image with respect to an original image acquired with a predetermined contrast or brightness, extracting a dark portion from the bright image, extracting a bright portion from the dark image, and then composing the extracted dark portion image and bright portion image.

However, according to the image processing technology using the contrast adjustment method disclosed in the above publication, when a back-scattered electron image of a pattern containing materials with close atomic numbers is acquired, the image has a small contrast difference.

As one of the ways to increase contrast partly so as to provide an image contrast difference, intermediate luminance emphasis is known. This technology, however, has the problem that when the luminance of various materials is expressed in a histogram, waveforms in the histogram are overlapped between the materials, so that the range for luminance emphasis cannot be properly set.

Thus, it is difficult to obtain high resolution according to the related art including the above technology. When the resolution is low during image observation, length measurement reproducibility, for example, is decreased.

SUMMARY

An object of the present invention is to provide a technology such that the resolution of a back-scattered electron image can be increased.

The present invention proposes methods and apparatuses such that, in order to provide a contrast difference so that high image resolution can be obtained, an index value for partial luminance emphasis is determined on the basis of the atomic number, and the contrast/brightness of an image is adjusted.

According to an aspect of the present invention, an image processing apparatus that performs an image process using a back-scattered electron image as an input image includes a material peak detection unit that determines a peak luminance value with a peak of a frequency of a luminance histogram based on a luminance value obtained for each measurement position by using the input image as an input and information about material-dependent back-scattered electron generation efficiency, and that outputs the peak luminance value for each material; and an image information adjustment unit that emphasizes a material-dependent contrast on the basis of the input image and the peak luminance value for each material.

A signal peak value for each material is calculated from the input image. The peak value for each material may be calculated by theoretically calculating the back-scattered electron generation efficiency by a Monte Carlo simulation, and performing deconvolution on the luminance histogram on the basis of information about the generation efficiency.

Even when two or more materials with close atomic numbers are present in the same field of view in a back-scattered electron image, a contrast difference can be provided by implementing luminance conversion (deconvolution) depending on the atomic numbers of the materials, whereby the resolution of the back-scattered electron image can be increased. Thus, the material-dependent contrast can be provided to the back-scattered electron image.

Preferably, the image processing apparatus may include a luminance information extraction unit that acquires and outputs a maximum value and a minimum value of the luminance of the input image by detecting luminance information of the input image as an input. The image information adjustment unit may emphasize the contrast of the input image on the basis of the peak luminance value from the material peak extraction unit and the maximum value and the minimum value of the luminance from the luminance information extraction unit.

Further, in addition to the emphasis of the material-dependent contrast, emphasis of contrast depending on a light source condition may be performed.

The emphasis process for the material-dependent contrast may be performed only upon failure to detect a pattern when an image is acquired by pattern detection.

Preferably, the image processing apparatus may include an interface enabling the selection of the material for luminance conversion.

According to an embodiment of the present invention, an electron microscope apparatus includes the image processing apparatus with any of the above configurations.

According to another aspect of the present invention, an image processing method for performing an image process using a back-scattered electron image as an input image includes a material peak detecting step of determining a peak luminance value with a peak of a frequency of a luminance histogram based on a luminance value obtained for each measurement position by using the input image as an input and information about material-dependent back-scattered electron generation efficiency, and outputting the peak luminance value for each material; and an image information adjustment step of emphasizing a material-dependent contrast on the basis of the input image and the peak luminance value for each material.

According to an embodiment, the image processing method may include a luminance information extraction step of acquiring and outputting a maximum value and a minimum value of the luminance of the input image by detecting luminance information of the input image as an input. The image information adjustment step may include emphasizing the contrast of the input image on the basis of the peak luminance value determined in the material peak extraction step and the maximum value and the minimum value of the luminance determined in the luminance information extraction step.

According to another aspect of the present invention, a program for causing a computer to perform the image processing method may be provided.

Effects of the Invention

According to an embodiment of the present invention, an optimum contrast can be set even for an image without a contrast difference between materials with close atomic numbers, whereby the resolution of a back-scattered electron image can be increased.

DESCRIPTION

In the following, an image processing technology for adjusting a back-scattered electron image for optimum brightness, particularly an image processing technology including a contrast/brightness adjustment technology, in the case of application to a scanning electron microscope system will be described with reference to the drawings. Materials that may be contained in the sample are basically known.

Figure 1:
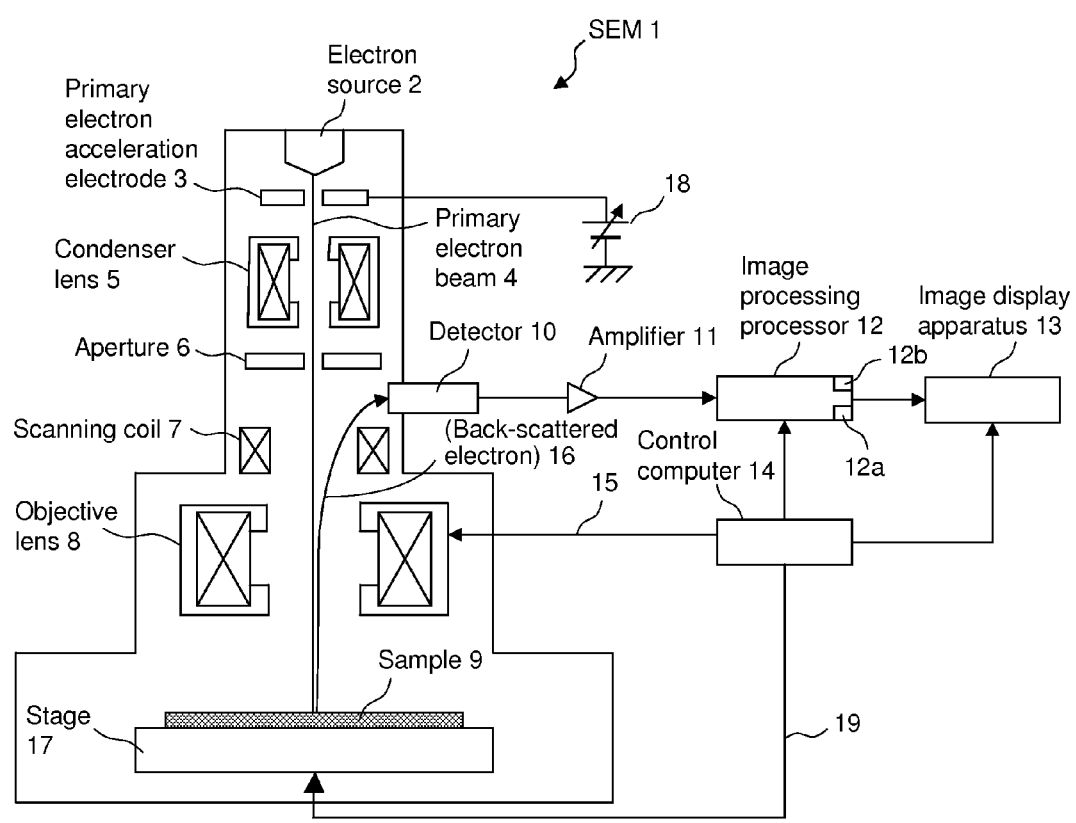
FIG. 1 illustrates a configuration example of a scanning electron microscope system according to an embodiment.

FIG. 1 illustrates a configuration example of a scanning electron microscope system according to an embodiment. In a scanning electron microscope (SEM) 1, a primary electron beam 4 produced by an electron source 2 is accelerated by a primary electron acceleration electrode 3 to which a voltage is applied from a primary electron acceleration power supply 18.

A condenser lens 5 is used for controlling the thickness of an electron probe and a probe current by controlling the current for the accelerated primary electron beam 4. The controlled primary electron beam 4 is narrowed by an aperture 6 and then scanned one- or two-dimensionally by a magnetic field generated by a scanning coil 7. An objective lens 8 is supplied with a control signal 15 from a control computer 14 and generates a magnetic field in accordance with the control signal 15 so that the one- or two-dimensionally scanned primary electron beam can be focused on the surface of a sample 9 on a stage 17.

From the sample 9 irradiated with the primary electron beam 4, secondary electrons and back-scattered electrons 16 are produced. The back-scattered electrons 16 are captured by a detector 10. Information of the captured back-scattered electrons is amplified by an amplifier 11, and an amplified signal is analog-to-digital converted in an image processing processor 12 into digital image data. The digital image data is supplied to an image display apparatus 13 and displayed as a sample image (field of view image) of a field of view region. The image processing processor 12 includes an image memory for storing digital image data, an image processing apparatus 12a that performs various image processes, and a display control apparatus 12b for display control.

The scanning electron microscope system illustrated in FIG. 1 also includes the function of forming a line profile based on the detected secondary electrons or back-scattered electrons, for example. The line profile is formed on the basis of the amount of electron detected by the detector 10 during the one- or two-dimensional scan of the primary electron beam 4, luminance information of a sample image, and the like. The line profile formed may be used for recognizing a pattern formed on the sample 9 or measuring the size thereof.

For example, when the size of a fine pattern and the like formed on the sample 9 is measured, the control computer 14 controls a drive mechanism for the stage 17 via the control signal 19 so that a measurement region can be irradiated with the primary electron beam 4, and determines the position or inclination of the stage 17 such that the primary electron beam 4 can vertically irradiate the pattern as a measurement object. The image processing apparatus 12a in the image processing processor 12 processes the digital image data detected from the region scanned with the primary electron beam 4 so as to form an image enabling the measurement of the size of the pattern.

Figure 2A:
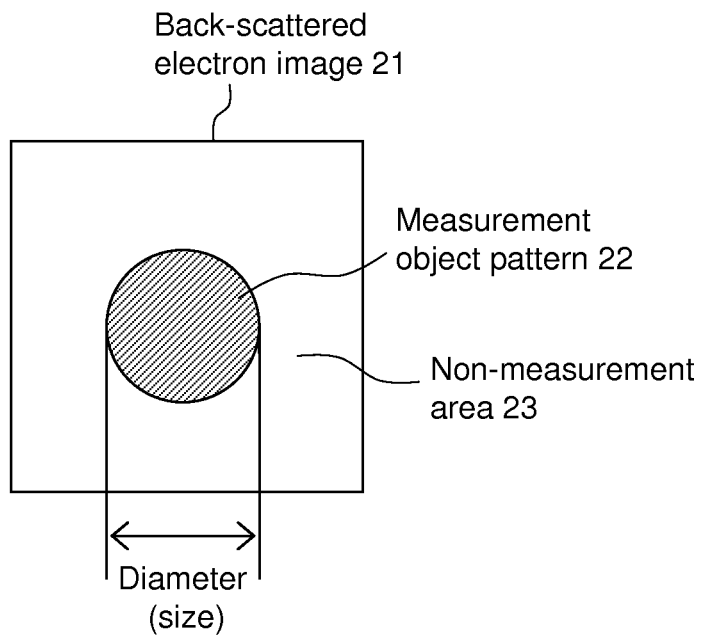
FIGS. 2A and 2B illustrate the measuring of the size of a back-scattered electron image.
Figure 2B:
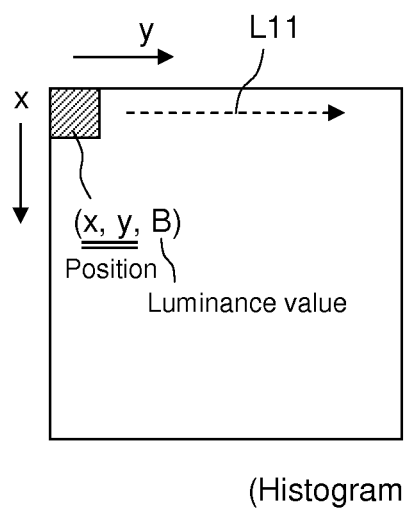

FIGS. 2A and 2B illustrate how the size of a back-scattered electron image is measured. As illustrated in FIG. 2A, when the size (such as diameter) of a measurement object pattern 22 in the back-scattered electron image 21 is to be measured, it is necessary to correctly determine the boundary between the measurement object pattern 22 and a non-measurement area 23. In practice, as illustrated in FIG. 2B, a two-dimensional surface of the sample surface is scanned in an x-direction and a y-direction to acquire an image and measure luminance B, whereby (x, y, B) is determined on a two-dimensional plane and a histogram can be created, as will be described later. The boundary in FIG. 2A may be determined on the basis of the contrast/brightness of each region. However, when the measurement object pattern 22 and the non-measurement area 23 have close atomic numbers, a contrast difference may not appear and the boundary may be obscure because the back-scattered electrons are dependent on the atomic number, resulting in a low image resolution.

First Embodiment

The image processing technology according to a first embodiment of the present invention will be described.

Figure 3:
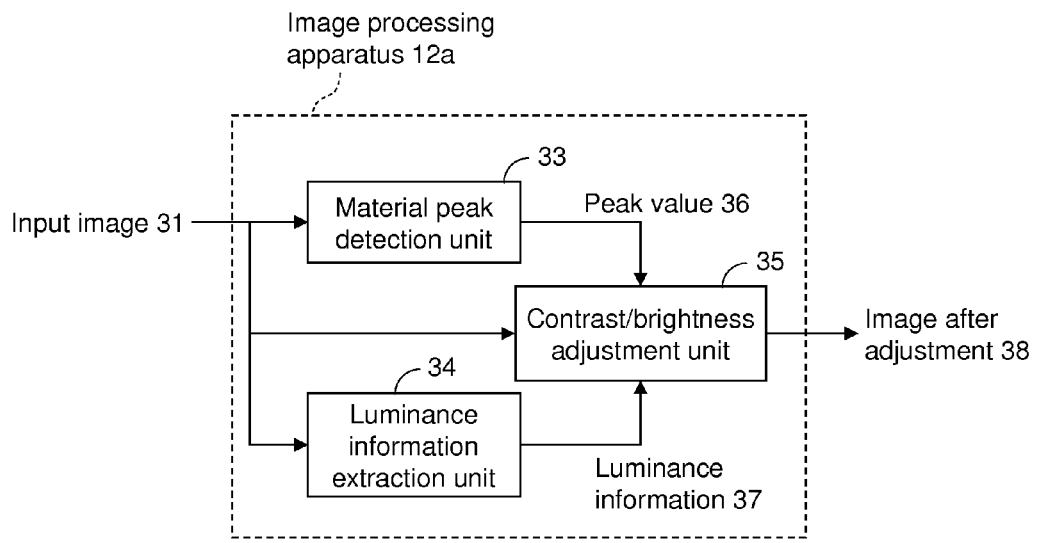
FIG. 3 is a functional block diagram of a configuration example of an image processing apparatus according to the present embodiment.

FIG. 3 is a functional block diagram of a configuration example of an image processing apparatus according to the present embodiment. As illustrated in FIG. 3, the image processing apparatus 12a according to the present embodiment includes a material peak detection unit 33, a luminance information extraction unit 34, and a contrast/brightness adjustment unit 35. The image processing apparatus 12a receives an input image 31 as an input, and outputs an image 38 after contrast/brightness adjustment.

The material peak detection unit 33 detects, on the basis of the input image 31, a peak value 36 which is defined as a luminance gradation value indicating a unique peak of a luminance histogram for each material. The luminance information extraction unit 34 extracts luminance information 37 on the basis of the input image 31. Based on the extracted peak value 36 and luminance information 37, the contrast/brightness adjustment unit (image information adjustment unit) 35 adjusts the peak value 36 outputted from the material peak detection unit 33 on the basis of the luminance information 37 from the luminance information extraction unit 34, thereby creating and outputting an adjusted image 38 that has been adjusted for contrast/brightness by intermediate luminance emphasis, for example, as will be described later. In the following, the respective units will be described in detail.

The material peak detection unit 33 calculates the signal peak value for each material from the input image 31. The peak value for each material may be calculated by theoretically calculating the back-scattered electron generation efficiency by a Monte Carlo simulation, for example, and then performing deconvolution on a luminance histogram on the basis of the generation efficiency information.

As an example, a mechanism for implementing deconvolution adapted to material according to the present embodiment, in addition to the generally known deconvolution depending on the condition of the light source (beam), will be described.

The deconvolution adapted to material according to the present embodiment involves implementing deconvolution depending on the material. More specifically, deconvolution is implemented depending on the thickness or size of the material, or the broadening of a signal source depending on the atomic number.

FIGS. 4(a) and 4(b) illustrate examples of a luminance histogram before and after a deconvolution process for a sample containing materials A, B, and C. In the luminance histogram prior to conversion, it is seen that the histogram has partial overlaps between the materials A, B, and C on the luminance axis. Preferably, these overlaps between the materials should be separated on the luminance axis after conversion as illustrated.

If deconvolution depending on the condition of the light source (beam) is $\sigma_{beam}$, and the deconvolution adapted to material according to the present embodiment is $\sigma_m$, the overall deconvolution $\sigma$ can be expressed by the following.

$$\sigma = \sqrt{\sigma_{beam}^2 + \sigma_m^2}$$

Figure 4:
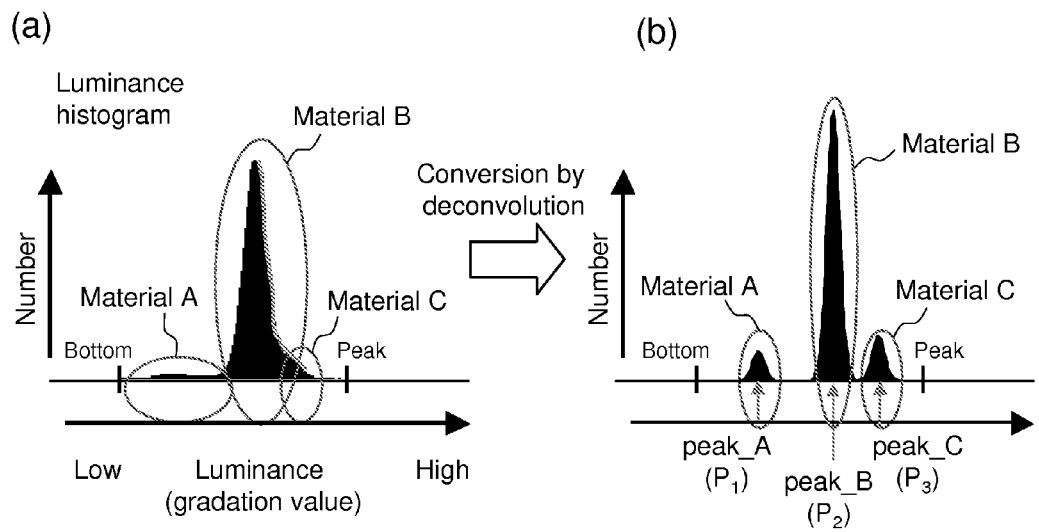
FIGS. 4(a) and 4(b) are examples of a luminance histogram before and after a deconvolution process in a sample containing materials A, B, and C.

The luminance histogram prior to conversion illustrated in FIG. 4 shows that the dispersion (manner of expansion of the tails) varies among the respective waveforms for the materials A, B, and C. Namely, $\sigma_m$ takes different values depending on the material. As deconvolution $\sigma_m$, one that is adapted to the peak of each material, i.e., the respective materials is applied. In other words, $\sigma_m$ may be $\sigma_{mA}$, $\sigma_{mB}$, or $\sigma_{mC}$, for example, depending on the material. Also, the range of application of deconvolution $\sigma_m$ is dependent on the dispersion of each material. For example, the range of application of deconvolution is n$\sigma$ from the peak position of each material. In this way, the luminance histogram after conversion by deconvolution (FIG. 4(b)) can be obtained.

Figure 5:
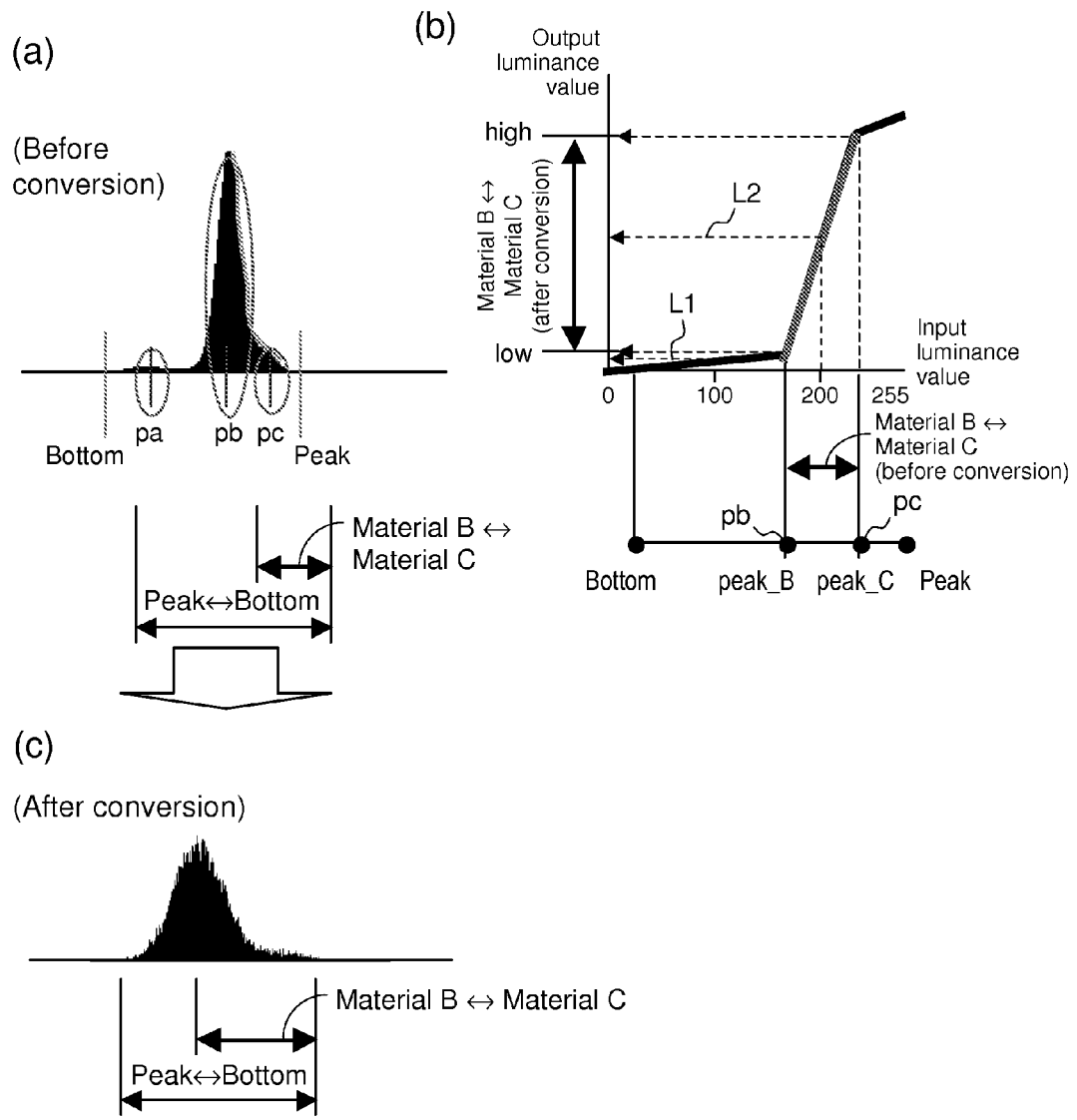
FIGS. 5(a), 5(b), and 5(c) illustrate the principle of an intermediate luminance emphasis process.

Meanwhile, FIG. 5 illustrates the principle of an intermediate luminance emphasis process. By scanning the sample surface to acquire position and luminance information as illustrated in FIG. 2A, a luminance histogram prior to the intermediate luminance emphasis process is obtained as illustrated in FIG. 5(a), which is similar to FIG. 4(a). The detailed flow of the process will be described later.

As illustrated in FIG. 5(a), the histogram is obtained between the bottom and the peak of the luminance value obtained by the luminance information extraction unit 34. Peak values pa, pb, and pc for the known materials of the sample 9 are determined in advance.

Then, as illustrated in FIG. 5(b), an input luminance value (horizontal axis) prior to adjustment is adjusted to an output luminance value (vertical axis) after adjustment. The adjustment by using such an S-shaped curve will be referred to as "intermediate luminance emphasis."

FIG. 5(b) indicates a function for adjusting (adjustment expression) the materials B and C as a graph with a line L1 and a line L2 with slopes set as adjustment coefficients. The expression may be used directly for the adjustment. In the present example, as illustrated in FIG. 5(b), the luminance values between pb and the bottom are adjusted in accordance with the line L1, and the luminance values between pb and pc are adjusted in accordance with the line L2.

In FIG. 5(a), a histogram prior to conversion is used, i.e., the histogram used is not the luminance histogram after conversion by deconvolution in the material peak detection unit 33 depending on the material. In practice, however, the peak values based on the luminance histogram after conversion illustrated in FIG. 4(b) are inputted to the contrast/brightness adjustment unit 35, so that the output more clearly indicates the material dependency.

By performing the adjustment according to FIG. 5(b) on the position-dependent luminance value determined as illustrated in FIG. 2B, the input luminance value prior to adjustment can be converted into an output luminance value after adjustment. The adjustment coefficients may be theoretical values, or set values based on past history, or values that can be inputted via an interface so that the respective materials can be separated appropriately.

For example, the function of FIG. 5(b) has the tendency such that, when the material B and the material C are adjusted, the slope increases from the peak value pb for the material B toward the peak value pc for the material C and decreases from the peak value pb for the material B in the opposite direction with respect to the peak value pc for the material C. The function may be a combination of quadratic functions, instead of a linear line. Preferably, for adjusting the material B and the material A, the horizontal axis of FIG. 5(b) may be reversed such that the slope increases toward pa.

FIG. 5(c) illustrates the luminance histogram after adjustment for the material B and the material C, which is extended along the luminance axis direction and has higher accuracy. This process is performed while scanning the sample with varying positions on the two-dimensional plane, as illustrated in FIG. 2A, so that eventually the frequency of the output luminance value after adjustment can be obtained.

An image process based on the principle illustrated in FIGS. 4 and 5 according to the present embodiment will be described in detail.

Figure 6:
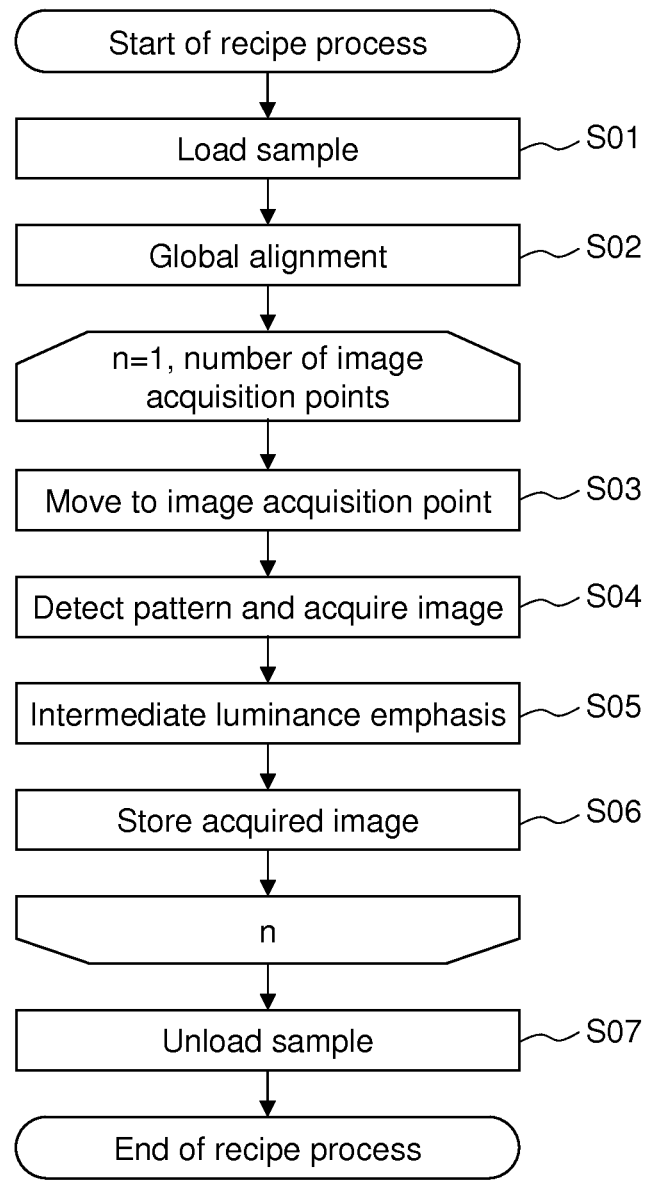
FIG. 6 is a flowchart of an image process according to the present embodiment, illustrating an example of the flow of an overall process including the intermediate luminance emphasis process.

FIG. 6 is a flowchart of an example of the flow of an overall image process according to the present embodiment, including the intermediate luminance emphasis process. Reference to other figures may be made as needed.

As illustrated in FIG. 6, first, the sample 9 is loaded into the scanning electron microscope (SEM) apparatus 1 (step S01), and global alignment is implemented (step S02).

In the process for each image acquisition point illustrated in FIG. 2B, first the stage 17 is moved to the point at which an image is acquired (position (x, y)) (step S03), the reference pattern for strictly identifying the image acquisition position is detected, and then an image is acquired (step S04). The acquired image is subjected to the intermediate luminance emphasis process according to the present embodiment (step S05).

Figure 7:
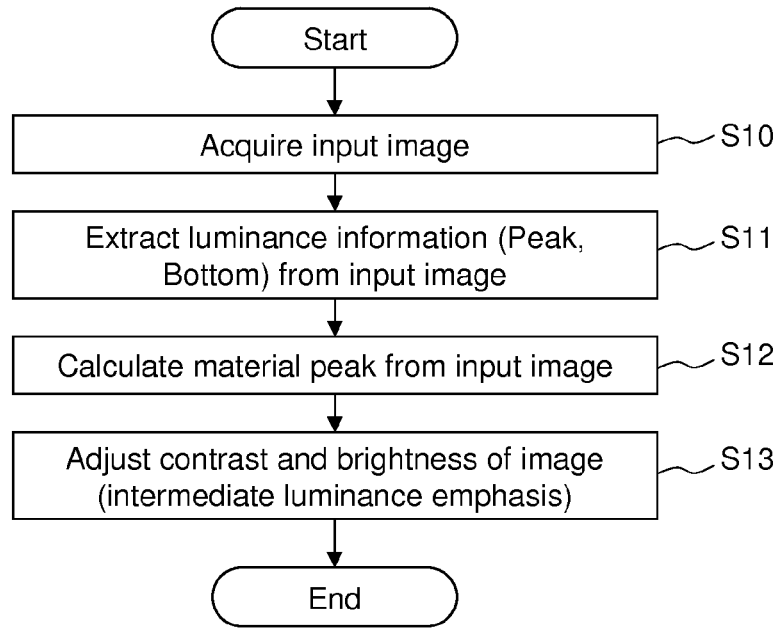
FIG. 7 is a flowchart illustrating an overview of the intermediate luminance emphasis process.

FIG. 7 is a flowchart illustrating an overview of the intermediate luminance emphasis process. As illustrated in FIG. 7, first, a back-scattered electron signal is acquired as an input image (step S10). Then, the luminance information extraction unit 34 extracts the luminance information of the image (Bottom, Peak) (step S11). The luminance information (Bottom, Peak) is the original data for the luminance histogram as illustrated in FIG. 4(a). Further, as illustrated in FIG. 2, the material peak calculation unit 33 calculates the peak value (pb, pc) for each material (step S12). Using the extracted luminance information and the calculated peak values as an input, the contrast/brightness adjustment unit 35 performs the intermediate luminance emphasis process as illustrated in FIG. 5 and thereby adjusts the contrast/brightness of the image (step S13). While FIG. 5(b) illustrates the example in which the emphasis process is performed between pb and pc, emphasis may be similarly provided between Bottom and pa, pa and pb, or pc and Peak.

Referring back to FIG. 6, after the contrast/brightness is adjusted by the process of FIG. 7, the acquired image after the image process is stored (step S06). After the process is completed for all of the image acquisition points, the sample is unloaded from the apparatus (step S07), and the process ends.

While the present embodiment has been described on the premise that the deconvolution depending on the condition of the light source (beam) and the deconvolution depending on the material according to the present embodiment are combined, the deconvolution according to the present embodiment may be independently performed.

Figure 8:
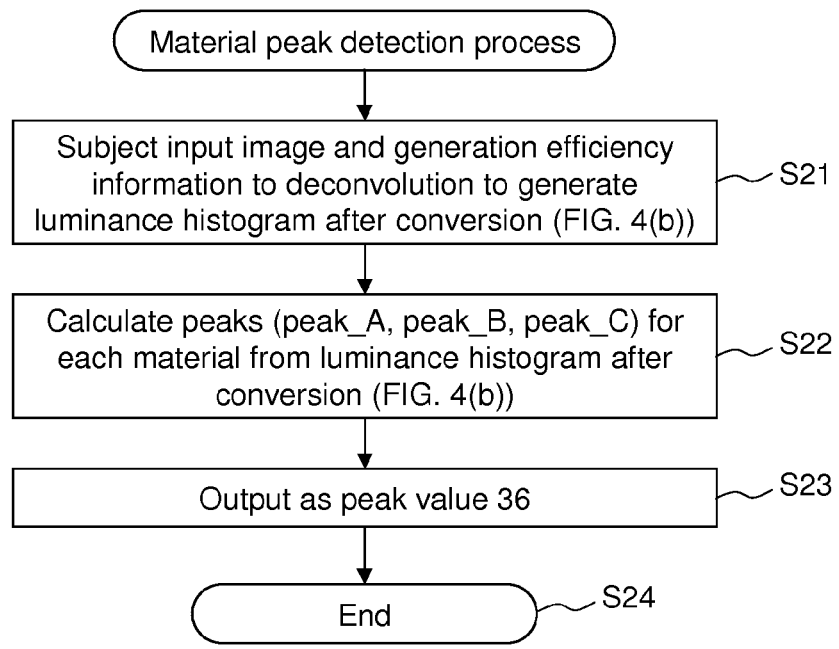
FIG. 8 is a flowchart illustrating the flow of a process in a material peak extraction unit.

FIG. 8 is a flowchart illustrating the flow of the process in the material peak extraction unit 33. As illustrated in FIG. 8, first, in step S21, the input image 31 and the conversion function (generation efficiency information) are deconvolved so as to generate the luminance histogram after conversion, as illustrated in FIG. 4(b). Then, in step S22, peak values for the respective materials, i.e., peak A (pa), peak B (pb), and peak C (pc) are calculated from the luminance histogram after conversion (FIG. 4(b)). In step S23, the peak values pa, pb, and pc calculated in step S22 are outputted to the contrast/brightness adjustment unit 35, and the process ends (step S24).

The luminance information extraction unit 34 acquires the maximum value Peak and the minimum value Bottom of the luminance of the input image by detecting the luminance information (Peak and Bottom) of the input image as illustrated in FIG. 4(a), and outputs the values to the contrast/brightness adjustment unit 35.

Figure 9:
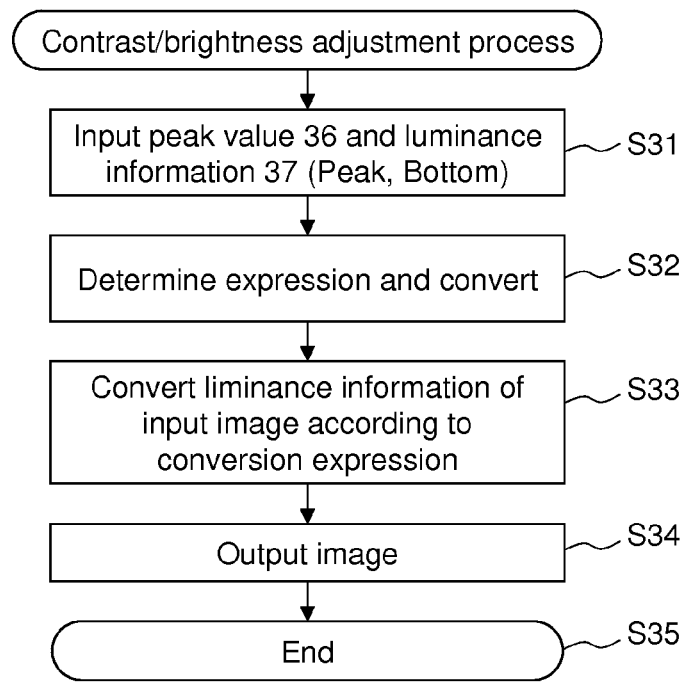
FIG. 9 is a flowchart illustrating the flow of a process in a contrast/brightness adjustment unit 35.

FIG. 9 is a flowchart illustrating the flow of the process in the contrast/brightness adjustment unit 35. As illustrated in FIG. 9, the contrast/brightness adjustment unit 35 receives the material peak information from the material peak extraction unit 33 and the maximum value Peak and the minimum value Bottom of the luminance of the luminance information input image from the luminance information extraction unit 34 (step S31). Using the peak values for the respective materials (pa, pb, pc) calculated by the material peak detection unit 33 and the luminance information (Peak, Bottom) extracted by the luminance information extraction unit 34 as inputs, the contrast/brightness adjustment unit 35 determines, in step S32, a conversion expression (function) illustrated in FIG. 5(b) in accordance with a user setting, for example, and converts the luminance information of the input image 31 according to the conversion expression in step S33. In step S34, an image having the luminance information converted in step S33 (FIG. 5(c)) is outputted, and the process ends (step S35). Namely, an image adjusted to the optimum contrast/brightness is outputted.

The adjustment process has been described with reference to an example in which, as a technique for providing a contrast difference to the peak value (boundary) of each material, intermediate luminance emphasis such that contrast can be partially expanded is applied.

While intermediate luminance emphasis will be described in the following as an example of the process in the contrast/brightness adjustment unit 35, the present invention is not particularly limited to intermediate luminance emphasis.

As described above, by using the image processing technology according to the present embodiment, conversion by material-dependent deconvolution is performed to emphasize material dependency, whereby a luminance distribution that has been subjected to an emphasis process is generated, so that the identification of material-dependent regions of an image can be facilitated.

The intermediate luminance emphasis process may be performed at all times, or a user may be allowed to make a setting as to whether the process is to be performed. Preferably, the intermediate luminance emphasis process may be performed only upon failure to detect a pattern when an image is acquired (step S04).

Second Embodiment

A second embodiment of the present invention will be described. The present embodiment relates to an apparatus with an interface for manually setting the intermediate luminance emphasis process. FIG. 10 illustrates an example of an interface screen according to the present embodiment.

Figure 10A:
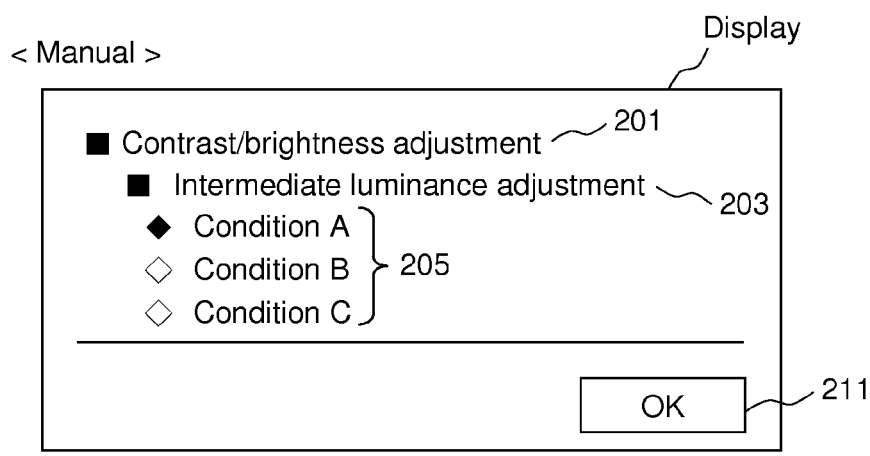
FIGS. 10A and 10B illustrate examples of an interface screen according to the present embodiment.

In the screen illustrated in FIG. 10A, whether the image process regarding contrast/brightness is to be performed on a manually acquired image is set by selecting an interface indicated by a sign 201 (in the illustrated example, selection is indicated by the blacked-out square). The screen also includes an interface 203 for selecting whether the intermediate luminance adjustment process is to be performed when the image process regarding contrast/brightness is performed. When intermediate luminance emphasis is to be implemented (as indicated by the blacked-out square), conditions 205 may be selected. The conditions 205 (such as conditions A to C) enable the setting as to the contrast between which materials is to be emphasized. Examples of the conditions include "emphasize the contrast between material A and material B", and "emphasize the contrast between material B and material C". When the material for emphasis is inputted, the function illustrated in FIG. 5(b), for example, is selected, and then the emphasis process is performed. By re-selecting the functions and the like, an appropriate process may be performed while comparing the results. The process is performed by pressing an OK button 211.

Thus, by simply selecting the pre-registered conditions freely, a desired back-scattered electron image in which the luminance between materials is emphasized can be obtained. By selecting the (x, y) in FIG. 2B, for example, the emphasis process may be performed locally.

Figure 10B:
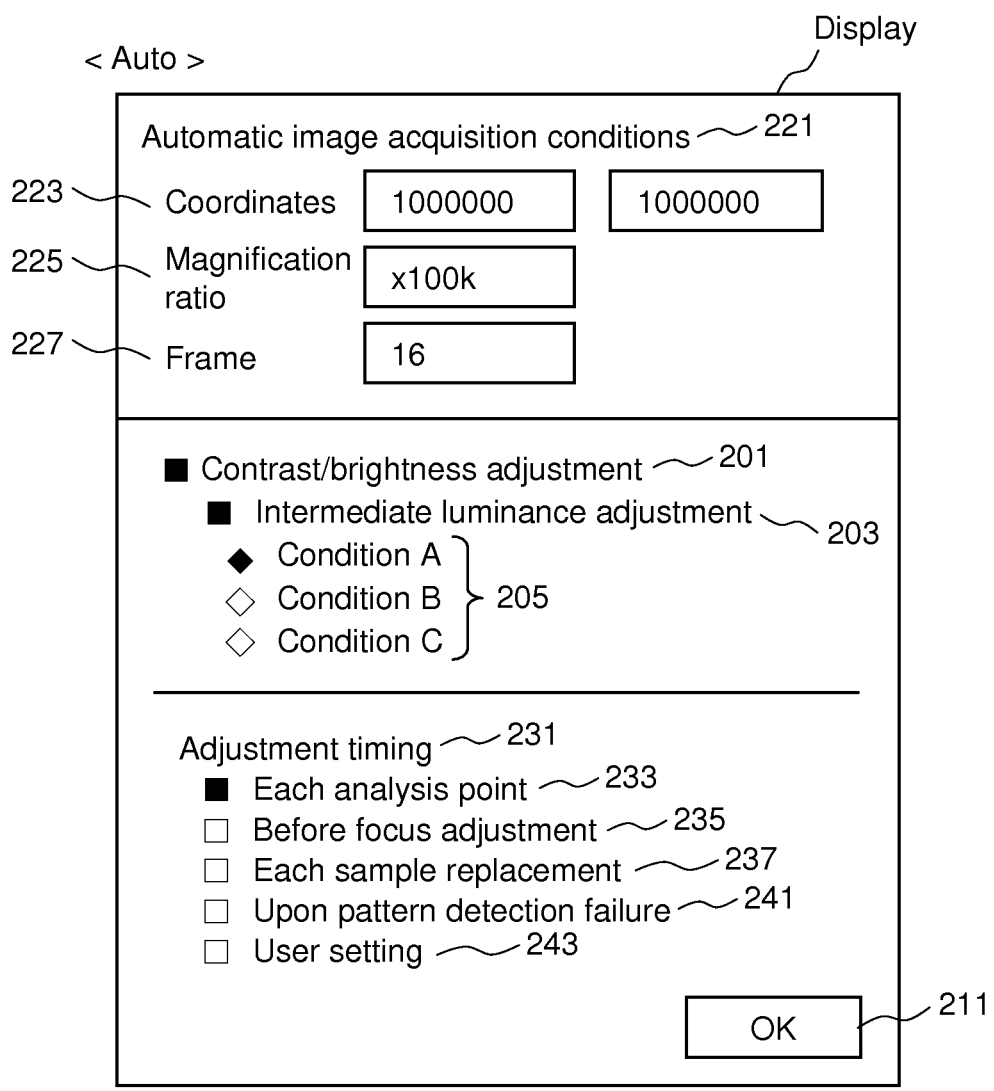

The screen illustrated in FIG. 10B is an example of an interface in automatic mode. As illustrated in FIG. 10B, after basic information such as coordinates 223, a magnification ratio 225, and the number of frames 227 is inputted in an automatic image acquire condition 221, selections are made, such as whether the contrast/brightness adjust 201 is to be performed and, when it is, whether the intermediate luminance adjustment process is to be performed, as in the case of the manually acquired image. Similarly, when the intermediate luminance emphasis process 203 is to be performed, the conditions 205 are selected. Then, the timing 231 for implementing the image contrast adjustment is selected from the alternatives 233, 235, 237, 241, and 243, for example, illustrated in FIG. 10B, and the automatic image acquire conditions are stored and implemented as a recipe (the OK button 211 is pressed).

In this way, regarding the image process according to the present embodiment, a desired process can be performed by a simple scan.

According to the first embodiment, when deconvolution adapted to material is implemented, deconvolution may be determined for each material in advance. Similarly, peak values for a plurality of materials may be acquired and then deconvolution may be acquired. By using deconvolution of a plurality of materials and the atomic numbers of the plurality of materials, an approximate equation or coefficient between the deconvolution and the materials may be calculated. For example, for an unknown material, deconvolution may be determined by substituting the atomic number of the unknown material in the approximate equation.

As described above, according to the present embodiment, an appropriate contrast can be set even for an image with no contrast difference between materials with close atomic numbers, so that the resolution of a back-scattered electron image can be increased.

The configurations and the like of the foregoing embodiments are not limited to those illustrated in the attached drawings and may be modified to the extent that the effects of the present invention can be obtained. Various modifications may be made without departing from the scope of the object of the present invention.

The constituent elements of the embodiments may be adopted or omitted as desired, and an embodiment with a resultant configuration is included in the present invention.

This application is based on the Japanese patent application JP2012-141083, all the content of which is incorporated in this application by reference.

INDUSTRIAL APPLICATION

An embodiment of the present invention may be used for an image processing apparatus.

REFERENCE SIGNS LIST

1 SEM
2 Electron source
3 Primary electron acceleration electrode
4 Primary electron beam
5 Condenser lens
6 Aperture
7 Scanning coil
8 Objective lens
9 Sample
10 Detector
11 Amplifier
12 Image processing processor
12a Image processing apparatus
13 Image display apparatus
14 Control computer
15 Control signal
16 Back-scattered electron
17 Stage
18 Primary electron acceleration power supply
19 Control signal
33 Material peak detection unit
34 Luminance information extraction unit
35 Contrast/brightness adjustment unit (image information adjustment unit)

What is claimed is:

1. An image processing apparatus that performs an image process using a back-scattered electron image as an input image, the image processing apparatus comprising:
a material peak detection unit configured to determine a peak luminance value with a peak of a frequency of a luminance histogram based on a luminance value obtained for each measurement position by using the input image as an input and information about material-dependent back-scattered electron generation efficiency, and configured to output the peak luminance value for each material; and
an image information adjustment unit configured to emphasize a material-dependent contrast on the basis of the input image and the peak luminance value for each material.

2. The image processing apparatus according to claim 1, further comprising:
a luminance information extraction unit configured to acquire and output a maximum value and a minimum value of the luminance of the input image by detecting luminance information of the input image as an input,
wherein the image information adjustment unit emphasizes the contrast of the input image on the basis of the peak luminance value from the material peak extraction unit and the maximum value and the minimum value of the luminance from the luminance information extraction unit.

3. The image processing apparatus according to claim 1, wherein, in addition to the emphasis of the material-dependent contrast, the contrast can be emphasized depending on a condition of a light source.

4. The image processing apparatus according to claim 3, wherein a contrast emphasizing process depending on the material is performed only upon failure to detect a pattern when an image is acquired.

5. The image processing apparatus according to claim 1, further comprising an interface configured to select the material for luminance conversion.

6. An electron microscope apparatus comprising the image processing apparatus according to claim 1.

7. An image processing method for performing an image process using a back-scattered electron image as an input image, the image processing method comprising:
   a material peak detecting step of determining a peak luminance value with a peak of a frequency of a luminance histogram based on a luminance value obtained for each measurement position by using the input image as an input and information about material-dependent back-scattered electron generation efficiency, and outputting the peak luminance value for each material; and
   an image information adjustment step of emphasizing a material-dependent contrast on the basis of the input image and the peak luminance value for each material.

8. The image processing method according to claim 7, further comprising:
   a luminance information extraction step of acquiring and outputting a maximum value and a minimum value of the luminance of the input image by detecting luminance information of the input image as an input,
   wherein the image information adjustment step includes emphasizing the contrast of the input image on the basis of the peak luminance value determined in the material peak extraction step and the maximum value and the minimum value of the luminance determined in the luminance information extraction step.

9. A non-transitory computer readable media storing a program for causing a computer to perform the image processing method according to claim 7.

* * * * *